(12) United States Patent
Goldfine et al.

(10) Patent No.: US 10,416,118 B1
(45) Date of Patent: Sep. 17, 2019

(54) MEASUREMENT SYSTEM AND METHOD OF USE

(71) Applicant: JENTEK Sensors, Inc., Waltham, MA (US)

(72) Inventors: Neil J Goldfine, Indian Harbour Beach, FL (US); Todd M Dunford, Amherst, MA (US); Scott A Denenberg, Newton, MA (US); Kevin P Dixon, Somerville, MA (US); Yanko K Sheiretov, Waltham, MA (US); Saber Bahranifard, Stoneham, MA (US); Stuart D Chaplan, Watertown, MA (US); Mark D Windoloski, Chelmsford, MA (US)

(73) Assignee: JENTEK Sensors, Inc., Marlborough, MA (US)

( * ) Notice: Subject to any disclaimer, the term of this patent is extended or adjusted under 35 U.S.C. 154(b) by 230 days.

(21) Appl. No.: 15/594,004

(22) Filed: May 12, 2017

Related U.S. Application Data

(60) Provisional application No. 62/336,442, filed on May 13, 2016.

(51) Int. Cl.
| | |
|---|---|
| *G01N 27/82* | (2006.01) |
| *G01N 27/90* | (2006.01) |
| *G01B 11/02* | (2006.01) |
| *A61B 5/0404* | (2006.01) |
| *G01N 27/04* | (2006.01) |
| *G01R 27/12* | (2006.01) |

(52) U.S. Cl.
CPC ....... *G01N 27/9073* (2013.01); *A61B 5/0404* (2013.01); *G01B 11/026* (2013.01); *G01N 27/04* (2013.01); *G01N 27/9046* (2013.01); *G01R 27/12* (2013.01)

(58) Field of Classification Search
CPC .... G01N 27/72; G01N 27/90; G01N 27/9046; G01R 33/10; G01R 33/0064; G01R 33/0093; G01R 33/0094
See application file for complete search history.

(56) References Cited

U.S. PATENT DOCUMENTS

| | | | | |
|---|---|---|---|---|
| 7,385,392 B2 * | 6/2008 | Schlicker | ............... | G01N 27/82 324/242 |
| 2016/0349214 A1 | 12/2016 | Goldfine et al. | | |

* cited by examiner

*Primary Examiner* — Minh N Tang
(74) *Attorney, Agent, or Firm* — Zachary M. Thomas

(57) ABSTRACT

A measurement system, its assembly and use are disclose. The system may include an instrument for making sensor measurements. The instrument has a substantially cylindrical housing. The shape and size allow the instrument to easily fit in an average hand enabling handheld operation. The housing houses a board stack of electronic boards. These electronics drive an electrical signal in at least one drive channel and measure responses from at least two sensing channels. These responses are provided to a processor for analysis. The instrument has a sensor connector that enables simultaneous electrical and mechanical attachment of an end effector.

9 Claims, 16 Drawing Sheets

MEASUREMENT SYSTEM AND METHOD OF USE

The present application claims priority under 35 U.S.C. § 119(e) to U.S. provisional patent application, U.S. Ser. No. 62/336,442, filed May 13, 2016, which is herein incorporated by reference in its entirety.

SUMMARY

In some aspects the inventions relates to the following:

A measurement system comprising an impedance instrument; a substantially cylindrical housing for the impedance instrument, the housing having an average radius between 0.5 and 1.5 inches; and an end-effector configured to attach to the impedance instrument at one end of the housing.

In some embodiments, of the measurement system the end-effector comprises an eddy-current sensor. In some embodiments the eddy-current sensor is an eddy-current sensor array. In some embodiments the end-effector comprises a capacitive sensor.

In some embodiments the substantially cylindrical housing comprises an alignment portion at the end of the housing to which the end-effector attaches, the end-effector comprises a sensor with a flexible substrate material and a mechanical support, the sensor includes an electrical connector, the mechanical support has a mechanical connector, and the alignment portion is configured to engage the end-effector such that the electrical and mechanical connectors are attached in a single motion. In some embodiments of the measurement system the single motion is a spinning motion. In some embodiments the portion comprises at least one alignment pin.

Another aspect relates to an apparatus comprising a housing that is substantially cylindrical; a board stack of at least two electronic boards within the housing, the board stack configured to drive an electrical signal in at least one drive channel and measuring responses from at least two sensing channels; a communication module configured to provide the responses to a processor; and an instrument side sensor connector, located at one end of the housing, operably connected to the board stack.

In some embodiments the apparatus further comprises a sensor mechanism having a sensor and a threaded mechanical feature.

In some embodiments the apparatus further comprises a ring on the housing mechanically attaching the sensor mechanism, the ring having a retention plate with a pin for aligning a sensor side sensor connector with the instrument side sensor connector. In some embodiments the sensor mechanism is secured to the housing by the ring mating the sensor side sensor connector with the instrument side sensor connector such that an insertion between connectors is between 20% and 80% of a wipe length associated with said connectors.

In some embodiments the housing comprises a cover section having a first hole for a display; and a structural section having a plurality of mounting holes, the board stack mechanically secured to the plurality of mounting holes via fasteners. In some embodiments the apparatus further comprises an energy storage device for powering the apparatus, and wherein the board stack includes an energy storage device management circuit, and the housing further comprises a bottom cover section securing the energy storage device.

In some embodiments the housing further comprises a third section having side panels running along a longer dimension of the board stack and a crossing plate configured to channel heat away from temperature sensitive components, the crossing plate fit between a first and a second electronics board in the board stack.

In some embodiments the apparatus further comprises a gap pad adhered to the crossing plate and contacting at least one component on the first electronics board.

In some embodiments the apparatus further comprises a lanyard connected to the substantially cylindrical housing.

In some embodiments the outer diameter of the housing is less than 2.5 inches.

In some embodiments the processor is mounted on a board within the board stack. In some embodiments the processor is external to the housing.

In some embodiments the instrument side sensor connector includes pins for connecting an encoder.

In some embodiments the apparatus further comprises a mechanical connector at a same end of the housing as the instrument side sensor connector, the mechanical connector configured to attach an end effector containing a sensor to the housing while simultaneously engaging connection of the sensor to the sensor connector.

In some embodiments the electrical signal is a voltage.

In some embodiments the electrical signal is a current.

Another aspect relates to a method for assembling a substantially cylindrical apparatus comprising acts of: aligning mounting holes of a first electronics board with mounting holes on a structural section of a housing; attaching a plurality of male-male standoffs to respective mounting holes on the structural section securing the first electronics board; aligning mounting holes of an electromagnetic shielding material to the plurality of male-male standoffs thereby placing the electromagnetic shielding material over a top surface of the first electronics board; aligning mounting holes of a second electronics board to the plurality of male-male standoffs, and securing an electrical connector of the second electronics board to a respective electrical connector of the first electronics board; providing a second section of the housing having side panels and a cross plate; attaching a thermally conductive gap pad to the cross plate; aligning the second section of the housing to at least one feature of the structural section of the housing; aligning mounting holes of a third electronics board to the plurality of male-male standoffs, and securing an electrical connector of the third electronics board to the electrical connector of the second electronics board; engaging a retention feature of a cover section of the housing to the second section of the housing; and securing a second feature of the cover section with a corresponding feature of the second section.

In some embodiment the method further comprises attaching a second cover section of the housing to the structural section.

In some embodiment the method further comprises attaching a ring with a retention plate to one end of the housing.

In some embodiment the method further comprises securing a switch cable to the structural section of the housing prior to aligning mounting holes of a first electronics board with mounting holes on a structural section of a housing.

Yet another aspect relates to A apparatus comprising: a structural section of a housing; a first electronics board having mounting holes aligned with mounting holes on the structural section of a housing; a plurality of male-male standoffs attached to respective mounting holes on the structural section thereby securing the first electronics board; an electromagnetic shielding material over a top surface of the first electronics board, the electromagnetic shielding material having mounting holes aligned to the plurality of male-male standoffs; a second electronics board having mounting holes aligned with the plurality of male-male standoffs; a second section of the housing having side panels and a cross plate; a thermally conductive gap pad attached to the cross plate; a third electronics board having mounting holes aligned with the plurality of male-male standoffs; and a cover section of the housing having a retention feature engaged to the second section of the housing, wherein, an electrical connector of the second electronics board is secured to a respective electrical connector of the first electronics board; an electrical connector of the third electronics board is secured to the electrical connector of the second electronics board; the second section of the housing is aligned with at least one feature of the structural section of the housing; a second feature of the cover section is secured with a corresponding feature of the second section; and the structural section, the second section, and the cover section of the housing form a substantially cylindrical shape.

Another aspect relates to an apparatus for measuring impedance, the apparatus comprising: a housing that is substantially cylindrical in shape, less than 3 inches in diameter and less than 12 inches in length; a module configured to apply a current to a first terminal and measure the impedance at a frequency; an analog to digital converter for digitally sampling data at a plurality of second terminals; a device electrically connected to the analog to digital converter to receive the digitally sampled data and using stored firmware to compute the two components of the impedance simultaneously; a power board for providing power to the analog to digital converter using point of load regulation.

In some embodiments the apparatus further comprises an electrical connector at one end of the housing; and a mechanical connector at a same end of the housing, the mechanical connector configured to attach an end effector containing a sensor to the housing while simultaneously engaging connection of the sensor to the electrical connector.

In some embodiments the electrical connector comprises an instrument side sensor connector and instrument side position measuring device connector, the end effector comprises a position measuring device and a foam layer attached to the sensor, and the sensor is a flexible sensor array having a drive conductor and a plurality of sensing elements;

In some embodiments the power board provides power to the analog to digital converter by digitally sampling the voltage at the analog to digital converter and adjusting the voltage at the power board to correct for losses.

In some embodiments the power board is configured to switch from Power over Ethernet to a battery power source if the Power over Ethernet power source is outside a specification.

In some embodiments the apparatus further comprises a sensor operably connected to the module to receive the current.

In some embodiments the frequency is a first frequency, and the module is further configured to simultaneously measure impedance at a second frequency.

In some embodiments each second terminal is a sensing element of an eddy-current sensor array, and where the current is applied to a drive conductor in the eddy current sensor array.

In some embodiments the apparatus further comprises a sensor connector at one end of the housing; wherein a conducting path between the sensing element and a sensor connector has no active electronics and is less than 2 feet in length.

In some embodiments the two components of the impedance are a real part and an imaginary part.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The inventors have recognized the need for providing high-performance, non-destructive testing (NDT) equipment in a highly-portable format. Other needs that can be met by certain disclosed embodiments of the measurement equipment include easily interchangeable sensor cartridges; a light-weight, handheld format; compatibility with robotic manipulators for inclusion as an end effector in a robotic tool caddy; and the like.

Figure 1:
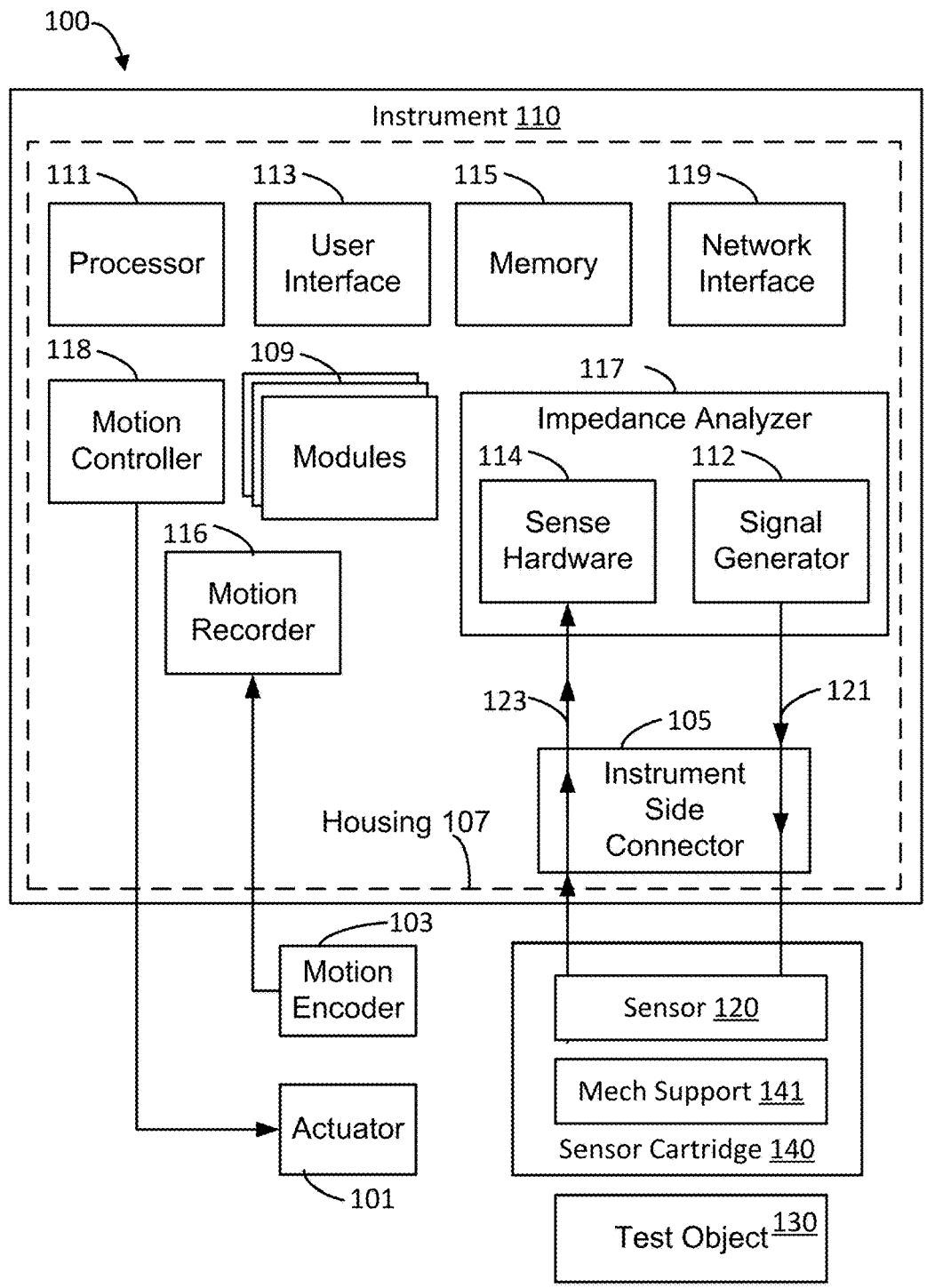
FIG. 1 is a system according to some embodiments.

FIG. 1 is a block diagram of a system 100 for inspecting a test object 130. System 100 includes an instrument 110 and a sensor cartridge 140. Instrument 110 may be housed in a housing 107; in some embodiments the housing is substantially cylindrical in shape. Sensor cartridge 140 has a rigid connector which interfaces both mechanically and electrically with an instrument side connector 105. Advantageously in some embodiments both the electrical and mechanical connections of sensor cartridge 140 engage simultaneously with connector 105. Sensor cartridge 140 also includes a flexible sensor 120, and a mechanical support 141 to which the sensor is attached. Instrument 110 is configured to provide excitation signals 121 to sensor 120 and measure the resulting response signals 123 of sensor 120. Response signals 123 may be measured and processed to estimate properties of interest, such as electromagnetic properties (e.g., conductivity, permeability, and permittivity), geometric properties (e.g., thickness, sensor lift-off), material condition (e.g., fault/no fault, crack size, corrosion depth, stress level, temperature), or any other suitable property or combination thereof (Sensor lift-off is a distance between the sensor and the closest surface of the test object for which the sensor is sensitive to the test object's electrical properties.) Some further aspects of some embodiments of sensor cartridge 140 are disclosed in U.S. Design patent application Ser. No. 29/603,805 filed on May 12, 2017 which is hereby incorporated by reference in its entirety.

Instrument 110 may include a processor 111, a user interface 113, memory 115, an impedance analyzer 117, and a network interface 119. Though, in some embodiments of instrument 110 may include other combinations of components. While instrument 110 is drawn with housing, it should be appreciated that instrument 110 may be physically realized as a single mechanical enclosure; multiple, operably-connected mechanical enclosures, or in any other suitable way. For example, in some embodiments it may be desired to provide certain components of instrument 110 as proximal to sensor 120 as practical, while other components of instrument 110 may be located at greater distance from sensor 120.

Processor 111 may be configured to control instrument 110 and may be operatively connected to memory 115. Processor 111 may be any suitable processing device such as for example and not limitation, a central processing unit (CPU), digital signal processor (DSP), controller, addressable controller, general or special purpose microprocessor, microcontroller, addressable microprocessor, programmable processor, programmable controller, dedicated processor, dedicated controller, or any suitable processing device. In some embodiments, processor 111 comprises one or more processors, for example, processor 111 may have multiple cores and/or be comprised of multiple microchips.

Memory 115 may be integrated into processor 111 and/or may include "off-chip" memory that may be accessible to processor 111, for example, via a memory bus (not shown). Memory 115 may store software modules that when executed by processor 111 perform desired functions. Memory 115 may be any suitable type of non-transient computer-readable storage medium such as, for example and not limitation, RAM, a nanotechnology-based memory, one or more floppy disks, compact disks, optical disks, volatile and non-volatile memory devices, magnetic tapes, flash memories, hard disk drive, circuit configurations in Field Programmable Gate Arrays (FPGA), or other semiconductor devices, or other tangible, non-transient computer storage medium.

Instrument 110 may have one or more functional modules 109. Modules 109 may operate to perform specific functions such as processing and analyzing data. Modules 109 may be implemented in hardware, software, or any suitable combination thereof. Memory 115 of instrument 110 may store computer-executable software modules that contain computer-executable instructions. For example, one or more of modules 109 may be stored as computer-executable code in memory 115. These modules may be read for execution by processor 111. Though, this is just an illustrative embodiment and other storage locations and execution means are possible.

Instrument 110 provides excitation signals for sensor 120 and measures the response signal from sensor 120 using impedance analyzer 117. Impedance analyzer 117 may contain a signal generator 112 for providing the excitation signal to sensor 120. Signal generator 112 may provide a suitable voltage and/or current waveform for driving sensor 120. For example, signal generator 112 may provide a sinusoidal signal at one or more selected frequencies, a pulse, a ramp, or any other suitable waveform.

Sense hardware 114 may comprise multiple sensing channels for processing multiple sensing element responses in parallel. Though, other configurations may be used. For example, sense hardware 114 may comprise multiplexing hardware to facilitate serial processing of the response of multiple sensing elements. Sense hardware 114 may measure sensor transimpedance for one or more excitation signals at on one or more sense elements of sensor 120. It should be appreciated that while transimpedance (sometimes referred to simply as impedance), may be referred to as the sensor response, the way the sensor response is represented is not critical and any suitable representation may be used. In some embodiments, the output of sense hardware 114 is stored along with temporal information (e.g., a time stamp) to allow for later temporal correlation of the data.

Sensor 120 may be an eddy-current sensor, a dielectrometry sensor, an ultrasonic sensor, or utilize any other suitable sensing technology or combination of sensing technologies. In some embodiments sensor 120 provides temperature measurement, voltage amplitude measurement, stain sensing or other suitable sensing modalities or combination of sensing modalities. In some embodiments, sensor 120 is an eddy-current sensor such as an MWM®, MWM-Rosette, or MWM-Array sensor available from JENTEK Sensors, Inc., Waltham, Mass. Sensor 120 may be a magnetic field sensor or sensor array such as a magnetoresistive sensor (e.g., MR-MWM-Array sensor available from JENTEK Sensors, Inc.), a segmented field MWM sensor, hall effect sensors, and the like. In another embodiment, sensor 120 is an interdigitated dielectrometry sensor or a segmented field dielectrometry sensor such as the IDED® sensors also available from JENTEK Sensors, Inc. Segmented field sensors have sensing elements at different distances from the drive winding or electrode to enable interrogation of a material to different depths at the same drive input frequency. Sensor 120 may have a single or multiple sensing and drive elements. Sensor 120 may be scanned across, mounted on, or embedded into test object 130.

In some embodiments, the computer-executable software modules may include a sensor data processing module, that when executed, estimates properties of the component under test. The sensor data processing module may utilize multi-dimensional precomputed databases that relate one or more frequency transimpedance measurements to properties of test object 130 to be estimated. The sensor data processing module may take the precomputed database and sensor data and, using a multivariate inverse method, estimate material properties. Though, the material properties may be estimated using any other analytical model, empirical model, database, look-up table, or other suitable technique or combination of techniques.

User interface 113 may include devices for interacting with a user. These devices may include, by way of example and not limitation, keypad, pointing device, camera, display, touch screen, audio input and audio output.

Network interface 119 may be any suitable combination of hardware and software configured to communicate over a network. For example, network interface 119 may be implemented as a network interface driver and a network interface card (NIC). The network interface driver may be configured to receive instructions from other components of instrument 110 to perform operations with the NIC. The NIC provides a wired and/or wireless connection to the network. The NIC is configured to generate and receive signals for communication over network. In some embodiments, instrument 110 is distributed among a plurality of networked computing devices. Each computing device may have a network interface for communicating with other the other computing devices forming instrument 110.

In some embodiments, multiple instruments 110 are used together as part of system 100. Such systems may communicate via their respective network interfaces. In some embodiments, some components are shared among the instruments. For example, a single computer may be used control all instruments. In one such embodiment multiple features, such as bolt holes or disk slots, are inspected simultaneously or in an otherwise coordinated fashion to using multiple instruments and multiple sensor arrays with multiple integrated connectors to inspect a component faster or more conveniently.

Actuator 101 may be used to position sensor cartridge 140 with respect to test object 130 and ensure suitable conformance of sensor 120 with test object 130. Actuator 101 may be an electric motor, pneumatic cylinder, hydraulic cylinder, or any other suitable type or combination of types of actuators for facilitating movement of sensor cartridge 140 with respect to test object 130. Sensor cartridge 140 may be positioned manually in some embodiments, while still other embodiments a combination of actuators and manual positioning may be used. For scanning applications where sensor 120 moves relative to test object 130, it is not critical whether sensor 120 or test object 130 is moved, or if both are moved to achieve the desired scan. Scanning may be performed in a contact or noncontact manner. For contact sensors, one embodiment includes a plastic shuttle or metal shuttle that is shaped similarly to the surface being inspected, with a flexible layer such as foam which is attached to the shuttle with an adhesive or other means, and with the sensor mounted to the foam. In some applications the foam or flexible layer is not included and the sensor is mounted directly to the plastic or other material shuttle.

Actuators 141 may be controlled by motion controller 118. Motion controller 118 may control sensor cartridge 140 to move sensor 120 relative to test object 130 during an inspection procedure. In one embodiment, a flexible lead is used to coil on a shaft to enable rotation of a sensor within a hole. In one such embodiment a gain stage of the electronics are located on a rotating mechanism that rotates with the sensor to improve performance. In another embodiment the entire instrument is rotated with sensor cartridge 140.

Regardless of whether motion is controlled by motion controller 118 or directly by the operator, position encoders 143 of fixture 140 and motion recorder 116 may be used to record the relative positions of sensor 120 and test object 130. This position information may be recorded with impedance measurements obtained by impedance instrument 117 so that the impedance data may be spatially registered.

Some further embodiments of system 100 are disclosed in U.S. patent application Ser. No. 15/030,094 filed Apr. 18, 2016 (U.S. published application No. 2016/0274060) which is hereby incorporated by reference in its entirety.

Figure 2:
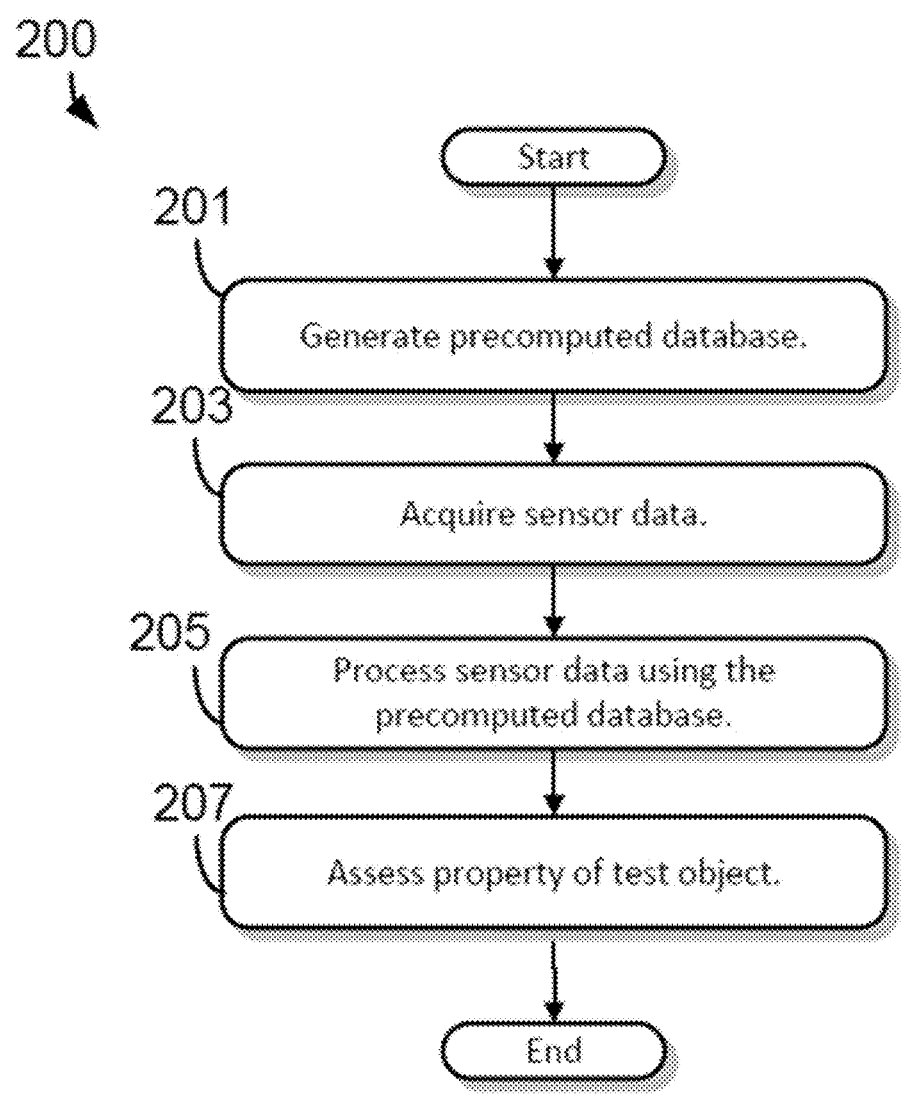
FIG. 2 is a method for assessing the property of a test object according to some embodiments.

System 100 may be used to perform a method 200 for assessing a property of a test object, shown in FIG. 2.

At step 201 a precomputed database of sensor response signals is generated. The response signals generated may be predictions of the response signal 123 in FIG. 1 for a given excitation signal 121, sensor 120 and test object 103. Response signals may be generated for a variety of excitation signals, sensors/sense elements, and test objects, including variation in the position and orientation of the sensor and test object. For example, the precomputed database may be generated for multiple excitation frequencies, multiple sensor geometries, multiple lift-offs, and multiple test object properties (e.g., geometric variations, electromagnetic property variations). The precomputed database may be generated using a model of the system, empirical data, or in any suitable way. In some embodiments the model is an analytical model, a semi-analytical model, or a numeric (e.g., finite element) model.

At step 203, sensor data is acquired. The sensor data may be acquired, for example, using instrument 110. Sensor data may be a recorded representation of the response signal 123, excitation signal 121, or some combination of the two (e.g., impedance). In some embodiments, sensor data is acquired at a plurality of excitation frequencies, multiple sensors (or sensing elements), and/or multiple sensor/test object positions/orientations (e.g., as would be the case during scanning).

At step 205, the sensor data is processed using the precomputed database generated at step 201. A multivariate inverse method may be used to process the sensor data with the At step 207, a property of the test object is assessed based on the processing of the measurement data at step 205. The property assessed may be an electromagnetic property, geometric property, state, conditions, or any other suitable type of property. Specific properties include, for example and not limitation, electrical conductivity, magnetic permeability, electrical permittivity, layer thickness, stress, temperature, damage, age, health, density, viscosity, cure state, embrittlement, wetness, and contamination. Step 207 may include a decision making where the estimated data is used to choose between a set of discrete outcomes. Examples include pass/fail decisions on the quality of a component, or the presence of flaws. Another example it may be determined whether the test object may be returned to service, repaired, replaced, scheduled for more or less frequent inspection, and the like. This may be implemented as a simple threshold applied to a particular estimated property, or as a more complex algorithm.

By performing step 201 prior to step 205 it may be possible that steps 203, 205 and 207 may be performed in real-time or near-real-time. Though, in some embodiments, step 201 may be performed after step 203 such as may be the case when database generation was not possible prior to the acquisition of measurement data, and perhaps further exacerbated by the fact that the test object may be no longer available for measurement.

Having described method 200 it should be appreciated that in some embodiments the order of the steps of method 200 may be varied, not all steps illustrated in FIG. 2 are performed, additional steps are performed, or method 200 is performed as some combination of the above. While method 200 was described in connection with system 100 shown in FIG. 1, it should be appreciated that method 200 may be performed with any suitable system.

Figure 3A:
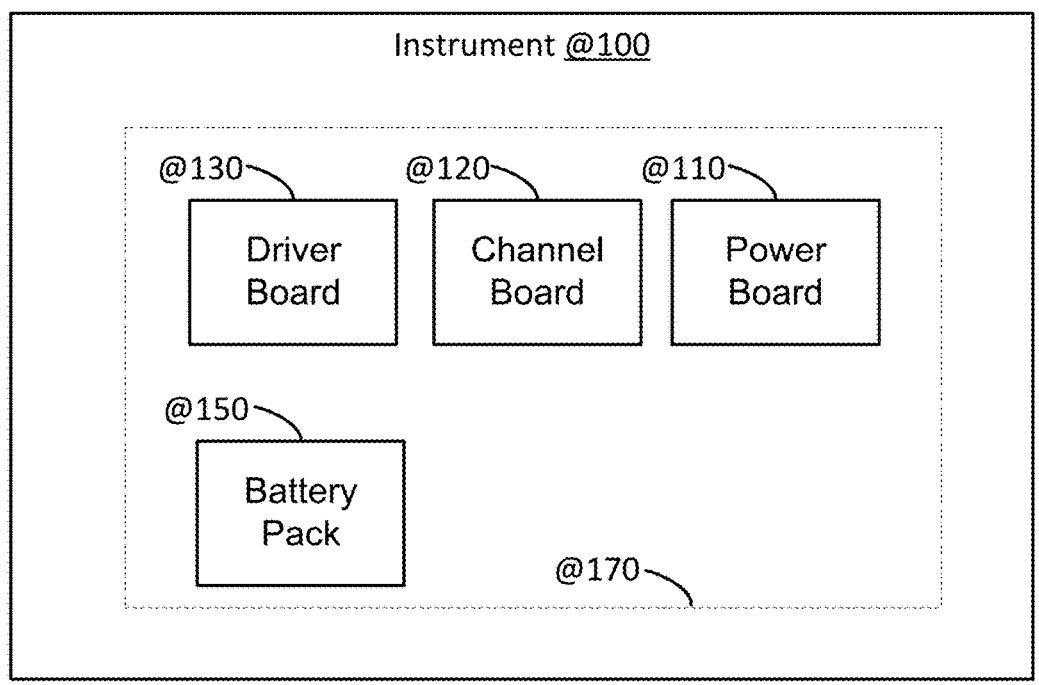
FIG. 3A-3D is an instrument according to some embodiments.

Turning now to FIG. 3A, an embodiment of instrument 110, referred to as instrument @100 is discussed.

Figure 3B:
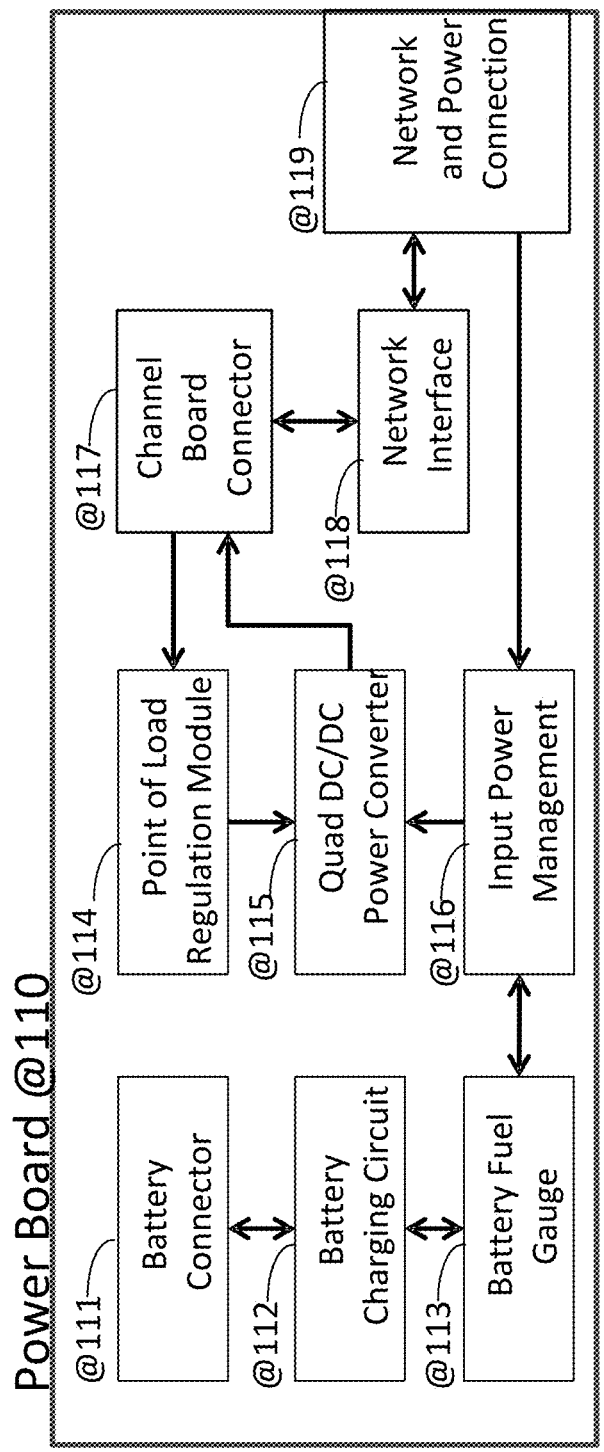

Instrument @100 has three distinct circuit boards which form a low profile electronics board stack. The boards in the stack are referred to as Power Board @110, Channel Board @120, and Driver Board @130. FIG. 3B shows a block diagram of Power Board @110 which receives both system power and a network connection from Network and Power Connection @119. The network connection is the means for the instrument to receive commands from, and send impedance measurement results to a host PC. The bi-directional data lines from the network correction interface with the instrument through Network Interface @118. Network Interface @118 handles the physical layer of the network stack translating the raw data from the network to logical packets that can be interpreted by the instrument. The translated signals from Network Interface @118 are routed through Channel Board Connector @117 where they can interface directly with the rest of Instrument @100's network stack.

The system power from Network and Power Connection @119 is first passed through the Input Power Management @116. Input power management @116 is responsible for ensuring that the power being provided to the system meets some basic specification before allowing it to pass to the rest of the system. The voltage of the input power is measured to ensure that it is neither too high nor too low for the system requirements. The current of the input power is also measured and can be cut off if it rises to a level that may damage the system. In addition to monitoring the quality of the input power, Input Power Management @116 also decided whether or not to power the system from a power source wired to Network and Power Connection @119 or battery pack @150. If wired power is available and within specification it may be the preferred power source, however, if the wired power source is not present or falls out of regulation the Input Power Management @116 automatically switches to battery pack @150 as the power source.

Battery Fuel Gauge @113 monitors the charging and discharging currents of battery pack @150 to keep track of its charge level and alert the instrument operator if the level falls below a certain threshold. Battery Charging Circuit @112 manages the charging profile of battery pack @150 to ensure battery safety and health. The circuit individually measures the voltages of each cell in the battery pack and avoids overcharging any one cell. Battery Charging Circuit @112 also manages the rate at which the battery is charged, charging faster when the battery is near empty and it is safe to do so while slowing the rate of charge when the battery is nearing full energy capacity. Battery Connector @111 passes charging and discharging current between battery pack @150 and instrument @100. Battery Connector @111 may be a spring pin type connector which makes electrical contact by applying sufficient force to keep the battery pack pressed up against the connector. Battery connector @111 also passes data lines to instrument @100's I2C communication bus to receive temperature information from battery pack @150.

Input Power Management @116 passes either wired or battery power to Power Converter @115, a quad DC/DC power converter, which regulates the main input power supply down to four lower voltages needed to power various electrical components. The Power Converter creates three fixed voltage supplies of 1.2V, 1.8V, and 3.3V as well as one variable voltage supply that ranges between 5V-10V. These voltage supplies are used to power most of the circuitry on the power board and all of the rest of the circuitry in the instrument. Additional filtering is provided to lower the electrical noise introduced by the switching power supplies implemented in Power Converter @115. Point of Load Regulation Module @114 implements point of load regulation in order to maintain a constant and precise voltage right at the point where it is needed on the other circuit boards. Without point of load regulation the voltages regulated at the output of Power Converter @115 would not be the same by the time they reached the components they were intended for. By implementing a feedback loop where the system is sampling the voltage supply next to the load instead of next to the regulator more accurate power supply regulation can be achieved.

Figure 4A:
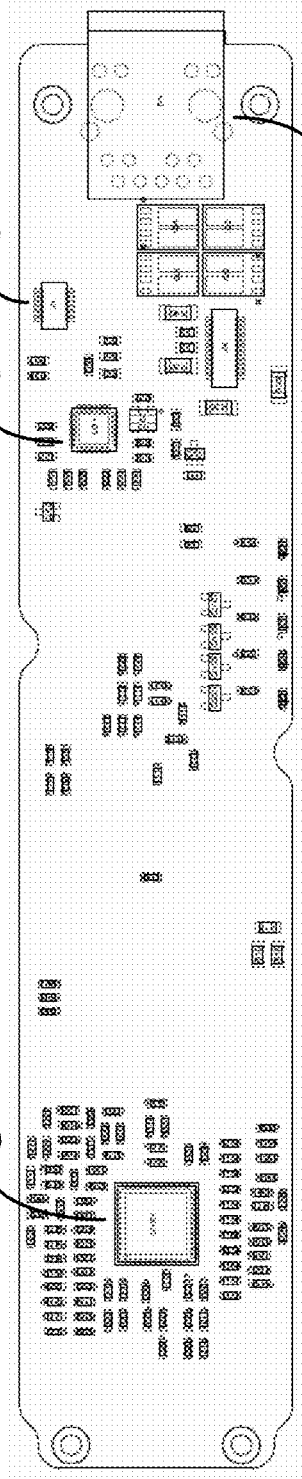
FIG. 4A-4D are electronics boards according to some embodiments.
Figure 4B:
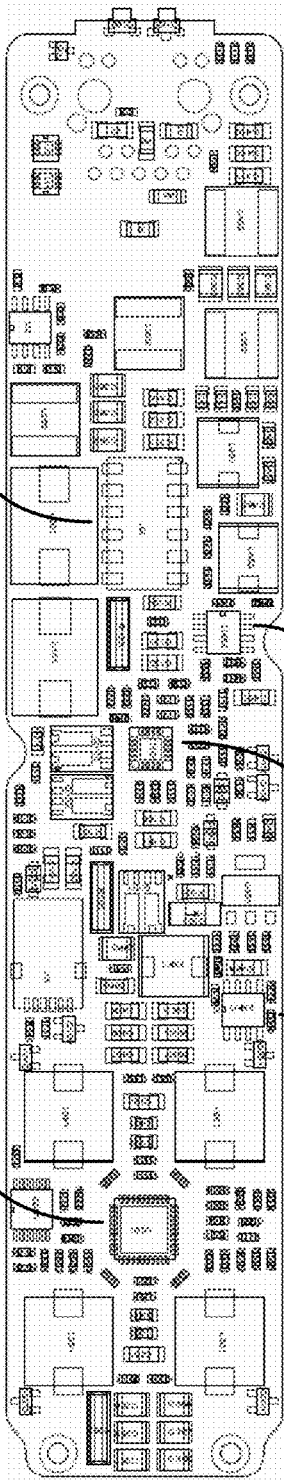

FIGS. 4A and 4B show the layout for one embodiment of power board @110.

Figure 3C:
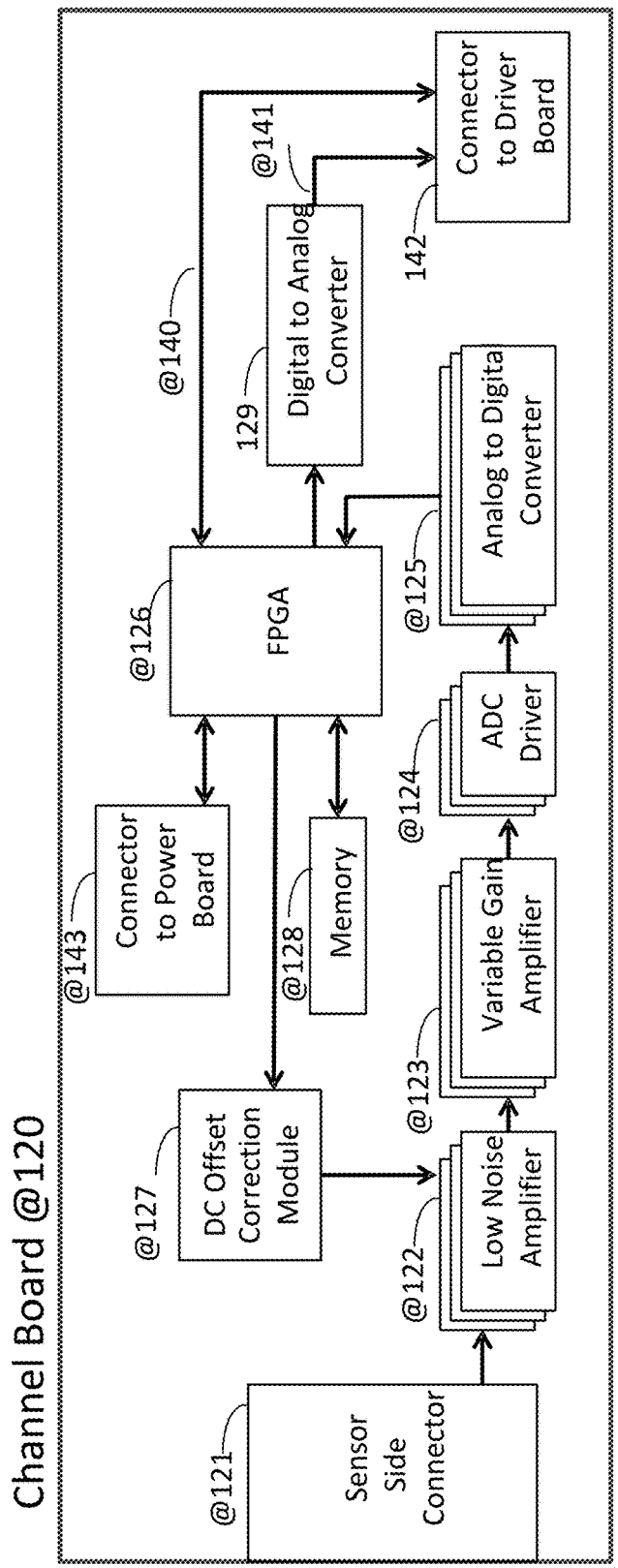

FIG. 3C shows a block diagram of Channel Board @120 which receives analog signal responses from Sensor Side Connector @121. Channel Board @120 supports seven sensor channels by providing seven fully independent and parallel hardware signal conditioning paths. The signals from the Sensor Side Connector @121 are received by 7 fully parallel Low Noise Amplifiers @122. The signals coming from the sensor are very low amplitude and care must be taken to introduce as little noise as possible into the signal at this point. The Noise Factor of the amplifiers is kept low by using high quality operational amplifiers and keeping the values of resistors as low as practical. DC Offset Correction Module @127 uses a digital to analog converter to apply a DC bias in order to cancel the DC offset introduced by Low Noise Amplifiers @122. DC Offset Correction is controlled via a digital feedback loop in which the existing DC offset is calculated at the end of the channel path and the appropriate cancellation voltage is calculated by FPGA @126 and applied back to Low Noise Amplifier @122 by DC Offset Correction @127. After the Low Noise Amplifier @122 stage, the next stage in the signal conditioning path is Variable Gain Amplifier @123. Variable Gain Amplifier @123 provides further signal amplification which can increase the signal to noise ratio of the sensor data. The value of the gain provided by this stage is set by FPGA @126 and is typically set as high as possible without exceeding the input voltage capabilities of the Analog to Digital Converter @125.

After the Variable Gain Amplifier @123 stage, the next stage in the signal conditioning path is ADC Driver @124. ADC driver @124 converts the single ended signal that comes from Variable Gain Amplifier @123 to a fully differential signal like Analog to Digital Converter @125 requires. ADC Driver @124 also regulates the output common mode voltage of the differential output signal to be equal to the reference voltage provided by Analog to Digital Converter @125. After ADC Driver @124 the sensor signals reach Analog to Digital Converter @125 which captures a digital representation of the sensor response which can be further processed by FPGA @126 and sent to the host PC as an impedance measurement. FPGA @126 receives the digitized data from Analog to Digital Converter @125 in a serialized format and must de-serialize it before performing digital signal processing on it. FPGA @126 implements a type of digital demodulation by multiplying the incoming digital signal by a reference waveform of the same frequency and then applying a digital low pass filter to obtain the real and imaginary part of the impedance measurement before transmitting the results to the Network Interface on the Power Board @110 via the Connector to the Power Board @143.

Memory @128 stores the program for FPGA @126 which must be reprogrammed into the FPGA every time the instrument powers on. Memory @128 can also be used to store information about the system including serial number, or firmware revision number. FPGA @126 also generates the digitized drive signal in real time using a cordic algorithm which eliminates the need to store digital representations of the drive signal at many different frequencies in memory. The digitized drive signal is then sent to the Digital to Analog Converter @129. The Digital to Analog Converter @129 takes the digital data from the parallel data bus of the FPGA @126 and converts it into a differential complimentary current signal @141 which is sent to the Driver Board via Connector to Driver Board @129. By varying the digital data sent to the Digital to Analog Converter @129 the FPGA @126 can drive the sensor at a variety of frequencies and amplitudes. FPGA @126 also controls the analog drive conditioning circuitry on the Driver Board through control signals @140. These control signals reach the Driver Board through Connector to the Driver Board @129 and are used to determine the amplitude of the signal that drives the sensor by enabling or disabling different gain stages in the drive path.

Figure 4C:
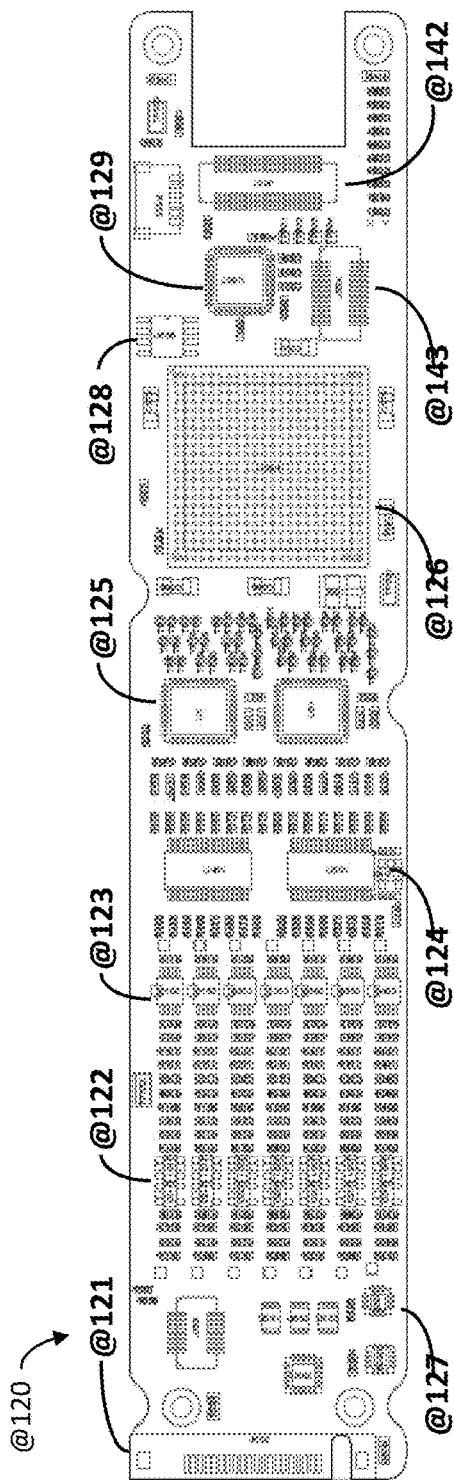

FIG. 4C shows the layout for one embodiment of Channel board @120.

Figure 3D:
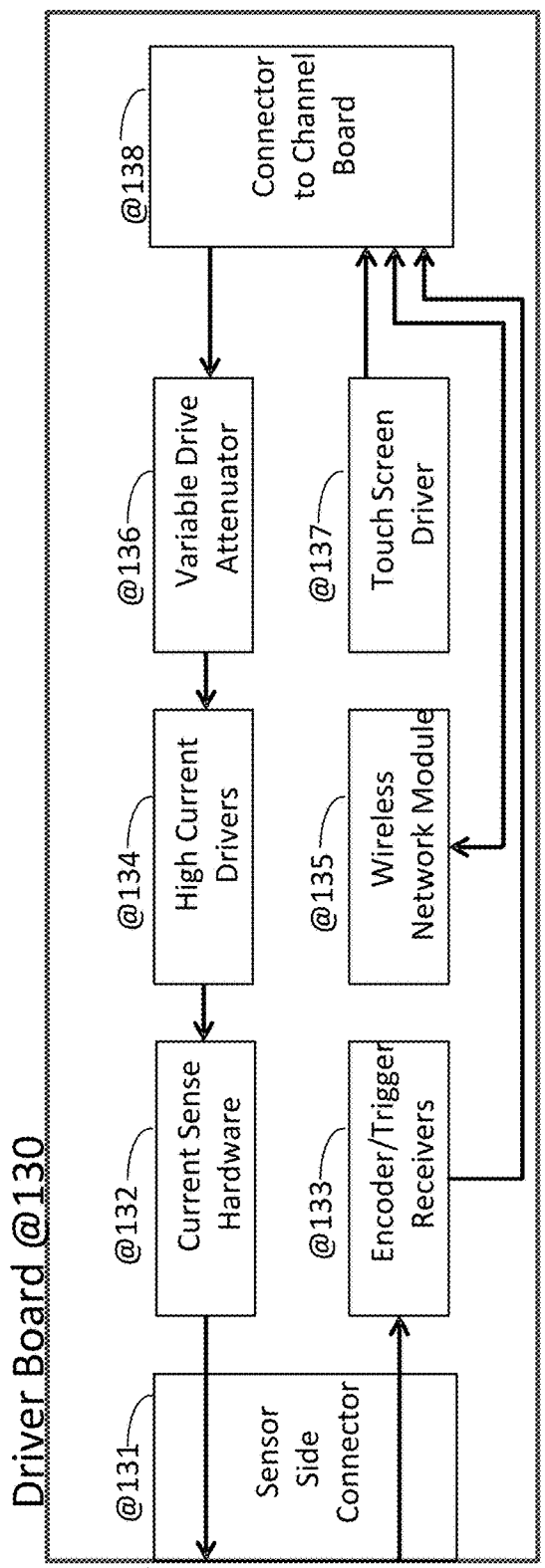

FIG. 3D shows a block diagram of Driver Board @130 which amplifies the low current drive signal from Channel Board @120 to create the high current signal which is needed to drive the sensor. The drive signal is brought to Driver Board @130 through Connector to the Channel Board @138 and is conditioned by Variable Drive Attenuator @136. To minimize the distortion of the drive signal and keep as much signal power as possible in the desired frequency, the signal from the Digital to Analog Converter is always kept at its maximum amplitude. This will result in the smoothest transitioning drive signal possible which will help decrease the harmonic distortion. However, it is not always desired to drive the sensor at the highest possible level, Variable Drive Attenuator @136 consists of a series of six switchable stages of operational amplifiers. At each stage the attenuator can either apply a fixed attenuation factor or buffer the signal to the next stage. By cascading stages in series in this manner, there are 64 unique drive levels that can be obtained through Variable Drive Attenuator @136.

The attenuated drive signal from Variable Drive Attenuator @136 is then amplified by the High Current Drivers @134. The high current drivers are capable of providing the current levels required to drive the sensor hard enough to induce a measurable response on the sense elements of the sensor. As a result of the high current the drivers will dissipate a large amount of power internally and require heat sinking to the housing of the instrument through a gap pad of high thermal conductivity. The drivers also use a dedicated power supply, the voltage of which can be varied over the entire operable range of the drivers. By lowering the voltage of the supply when the drivers are operating at a lower drive level the amount of wasted power in the system can be reduced, resulting in less heating of the instrument.

For converting the measured voltage of the sensor channels to an impedance value it is necessary to also measure the current that is being driven through the sensor. This is accomplished using the Current Sense Hardware @132 which resides between the high current drivers and Sensor Side Connector. The Current Sense Hardware @132 includes two types of current measurement circuitry which are intended for different frequency ranges of operation. The first type of current sense is an inductive current sense loop which feeds the high current drive signal through a primary loop on the printed circuit board and measures the voltage on a secondary loop which is proportional to the amount of current being driven into though the primary. This current sense type relies on inductive coupling between the primary and secondary loop which increases with frequency making it the more suitable choice for high frequency drives. The second type of current sense is a resistive type which feeds the high current drive signal through a highly precise, low value sense resistor and measures the voltage drop across the resistor. By using the measured voltage across the resistor and the known resistance value the current through the resistor can be calculated. Since the relationship between resistance, voltage, and current is independent of frequency, the resistive current sense is suitable for low frequency applications where the inductive current sense does not provide enough signal. Regardless of which current sense is used, the voltage being measured is conditioned by a signal path identical to those used for the sensor channels on Channel Board @120 before being measured by the Analog to Digital Converter on the Channel Board.

After the high current drive signal is measured by Current Sense Hardware @132 it travels through the Sensor Side Connector @131 to the external sensor. Sensor Side Connector @131 is also used to return signals from the external position encoders and triggers. Position Encoders are used in the system to keep track of the position of the sensor in scanning applications so measurements can be mapped to a specific location. Incremental position encoders are typically used which transmit a pulse every time the encoder wheel moves a specified angular distance. External triggers are used to allow external stimuli such as a button or foot pedal to send commands to the instrument such as take measurement, or calibrate. The signals from both the position encoders and the triggers are buffered by Encoder/Trigger Receivers @133 before being passed down to Channel Board @120 through the Connector to Channel Board @138. On the channel board the FPGA counts the number of pulses from the triggers and encoders since the last measurement and send the information to the host PC. The Encoder/Trigger Receivers @133 are responsible for level translation between the 5V logic encoders and the 3.3V logic FPGA as well as generally cleaning up the signals by removing any false indications.

Wireless Network Module @135 is a self-contained 802.11 b/g WLAN module which communicates with the FPGA through Connector to the Channel Board @138 through a SPI interface. The module can be used to connect to a wireless network and transmit measurement data when the wired network interface is not available. Wireless Network Module @135 has a chip antenna mounted on the printed circuit board but also offers the ability to connect an external antenna in case the range of the chip antenna is not sufficient. Touch Screen Driver @137 interfaces with a resistive touch panel that is overlaid on the TFT display of the instrument. The touch panel consists of two parallel sheets of a resistive film that alternately have a voltage applied across them by Touch Screen Driver @137 while the other has the voltage across it measured by the driver. When the films are pressed together the driver reads a voltage that is proportional to the location of the touch in either the X or the Y axis. Touch Screen Driver @137 interfaces with the FPGA using a SPI interface through Connector to Channel Board @138.

Figure 4D:
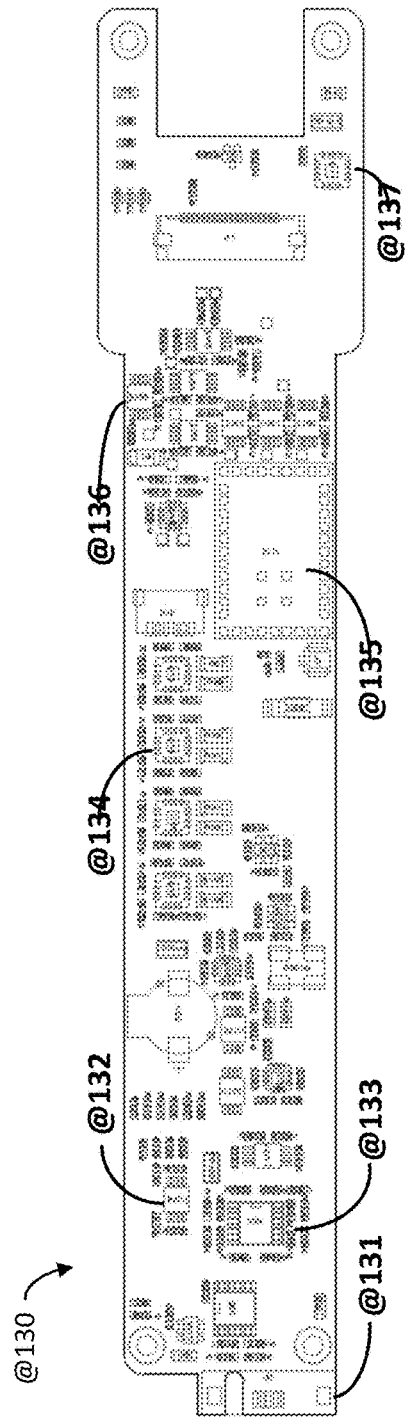

FIG. 4D shows the layout for one embodiment of Driver board @130.

It should be appreciated that aspects of instrument @100 may be implemented in ways described for instrument 110 and vice versa.

Figure 6A:
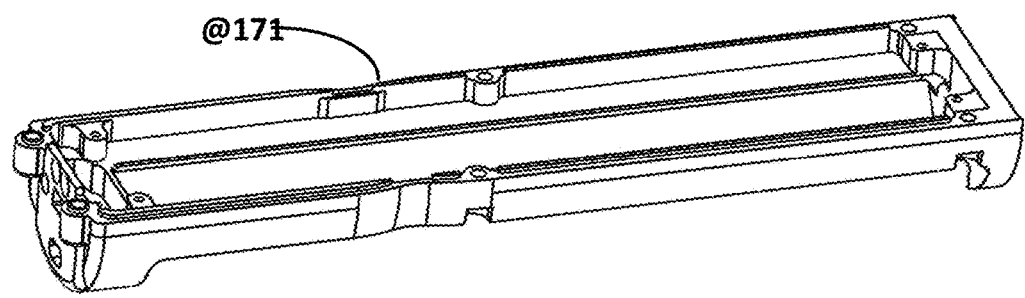
FIG. 6A-6P show assembly of an instrument and an assembled instrument according to some embodiments.
Figure 6B:
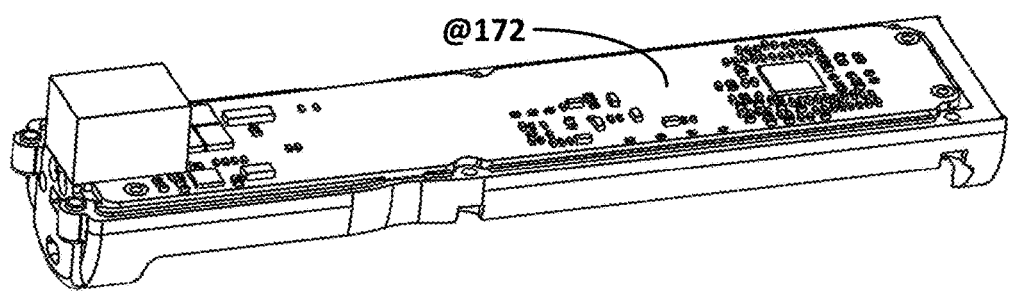

Instrument @100 has been configured in a mechanical housing suitable for handheld operation. In some embodiments the housing is substantially cylindrical in shape (as shown in FIG. 6O) having a diameter of approximately 1.5 inches to facilitate easy handheld operation by most adults. Such a geometry my accommodate comfort, function and ascetics for handheld operation. Embodiments having a substantially cylindrical shape may have an approximate diameter of less than 1, 2, or 2.5 inches in order to facilitate handheld operation. Some embodiments of the substantially cylindrical housing are disclosed in U.S. Design patent application Ser. No. 29/603,661 filed on May 11, 2017 which is hereby incorporated by reference in its entirety. A substantially cylindrical housing has no more than 30% variation in radius from a perfect cylinder along at least 60% of the length.

In some embodiments the surfaces of the housing are adapted for handling by a robot.

Figure 5:
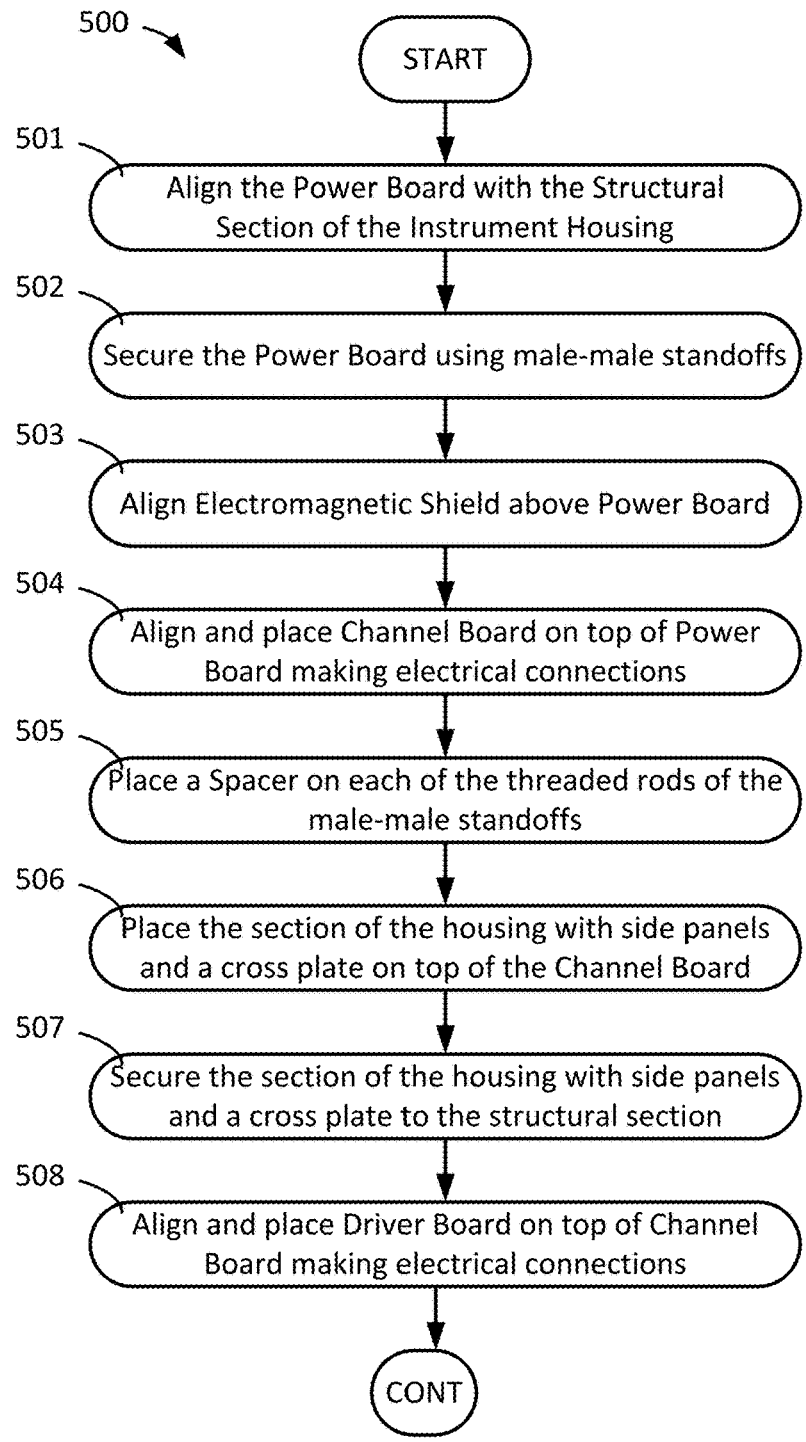
FIG. 5 is a method of assembling an instrument according to some embodiments.
Figure 5:
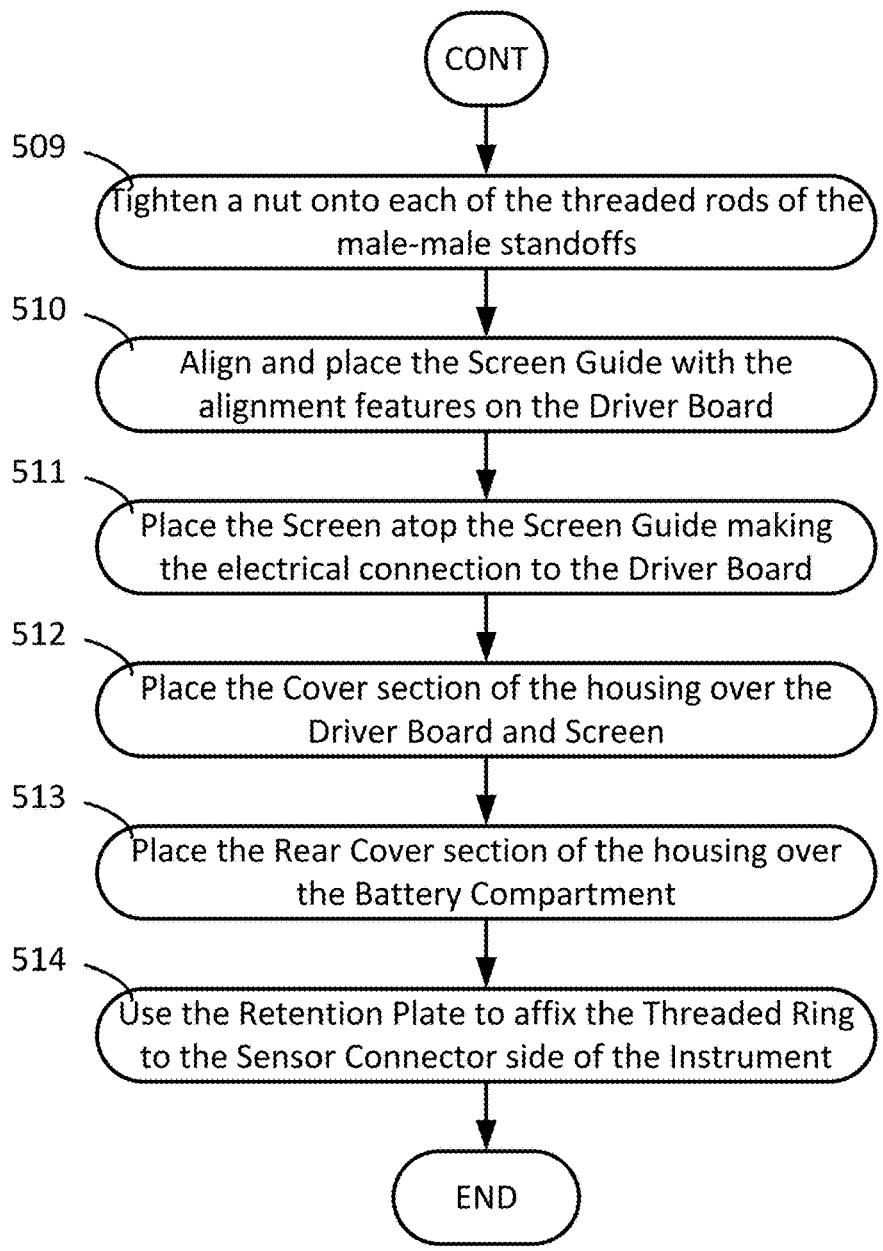

Turning to FIG. 5, a method 500 is described for assembling a portable instrument in a housing that is substantially cylindrical. Assembly is described in connection with the Instrument @100 embodiment (described in connection with FIG. 3), though it should be appreciated that method 500 may be used with any suitable embodiment of instrument 110.

At step 501 the power board @110 is fastened to the structural section @171 of the substantially cylindrical housing. The structural section of the housing is shown in FIG. 6A and serves as a base to build the stack of electronics boards upon.

The power board can be aligned with the structural section by matching the mounting holes on the board to the threaded screw holes on the structural section. There is also an asymmetrical keying in the outline of the electronics board to prevent the board from being placed in the wrong orientation. The aligned power board is shown in FIG. 6B.

Figure 6C:
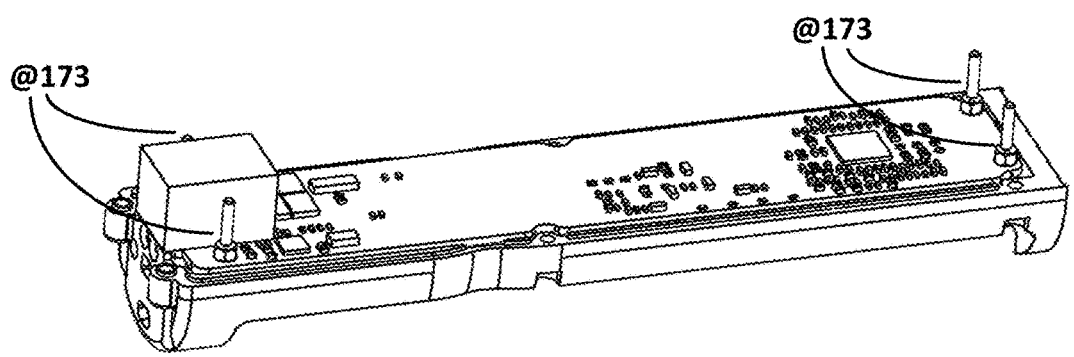

At step @502 Power Board @110 is secured to the structural section of the housing @171 in four locations with the use of male-male standoffs @172 as shown in FIG. 6C.

Figure 6D:
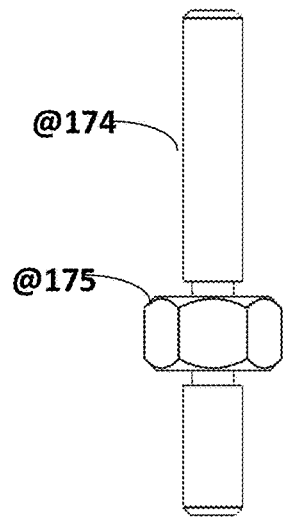

FIG. 6D shows the details of the male-male standoffs @172 which consist of a hexagonal nut @174 of a precise thickness to establish the spacing between the power board and the board that will mount above it. Protruding from the nut on either side is a threaded rod @173 used to mate with other features of the housing.

Figure 6E:
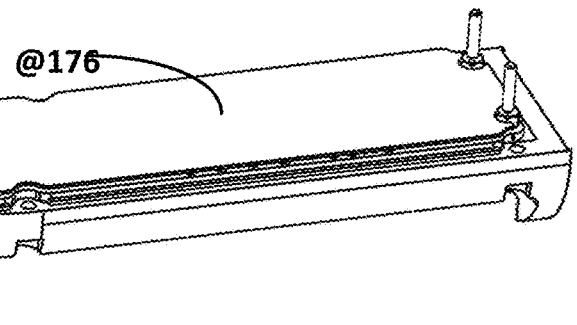

At step @503 an electrically insulated electromagnetic shield @175 is placed over the power board as shown in FIG. 6E. The shield is electrically insulated to prevent making inadvertent electrical connections across or between the two boards that the shield makes contact with. The shield is made of a highly magnetically permeable material which prevents the radiated noise from the power board from reaching the low noise sense hardware on the channel board. The shield has the same geometry as the power board, including the asymmetrical keying, so it can be visually aligned with the power board.

Figure 6F:
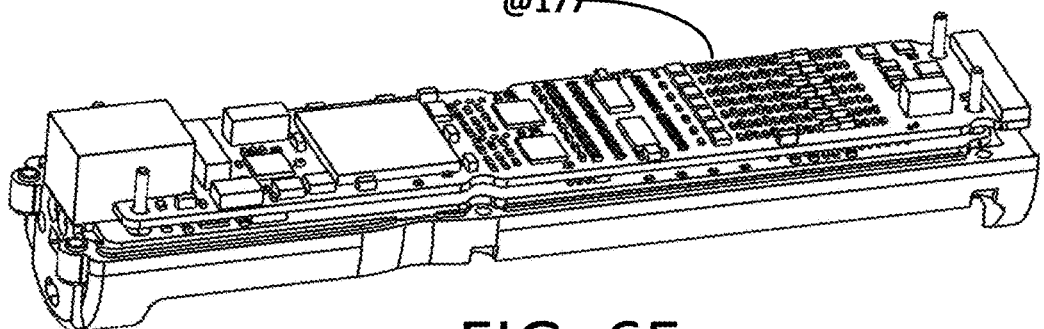

At step @504 Channel Board @120 is placed on top of the shield by aligning the mounting holes on the channel board with the protruding threaded rods from the male-male standoffs as shown in FIG. 6F. There are two sets of electrical connectors that need to mate in order for the boards to be fully in place. The nut portion of the male-male standoffs will keep the boards spaced precisely the distance required by the board to board connectors.

Figure 6G:
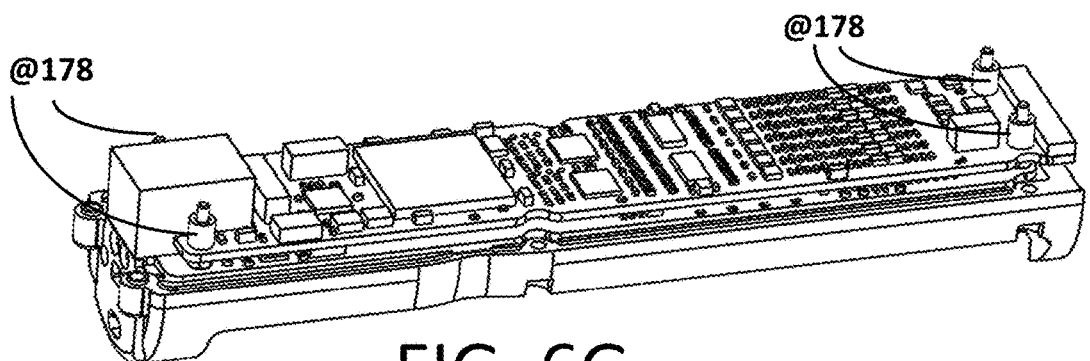

At step @505 spacers @176 are placed on each of the threaded rods on the male-male standoffs as shown in FIG. 6G. These spacers set the distance between the channel board and the driver board which is the next electronics board that will be added.

The next section of the housing that is added to the assembly consists of two side panels and a crossing plate @177. At step @506, before mounting it on the assembly, thermally conductive gap pad should be applied to the side of the cross plate that will face the channel board. The purpose of the cross plate is to provide a section of the housing to heat sink the electrical components that will generate the most heat to. The thermal gap pad has a very high thermal conductivity and serves as thermal connection between these components and the cross plate which will allow heat to be more easily removed from the components. The gap pad is adhesive to the housing section and will conform around the components on the channel board when pressure is applied.

At step @506 the section of the housing with the cross plate @177 should be placed on top of the channel board in the assembly. The housing section has keying features which align with asymmetrical cutouts on the sides of the electronics boards to prevent connection in the wrong orientation.

Figure 6H:
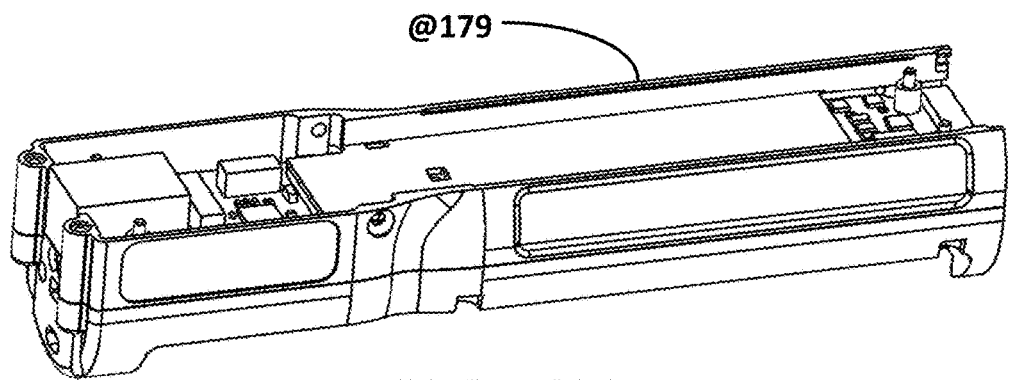

At step @507 the section of the housing with the cross plate @177 is secured to the structural section of the housing with the use of six screws. The tightening of these screws will press the gap pad down against the channel board components providing maximum contact surface area for the best thermal connection. The secured section of the housing with the cross plate @177 is shown in FIG. 6H.

Figure 6I:
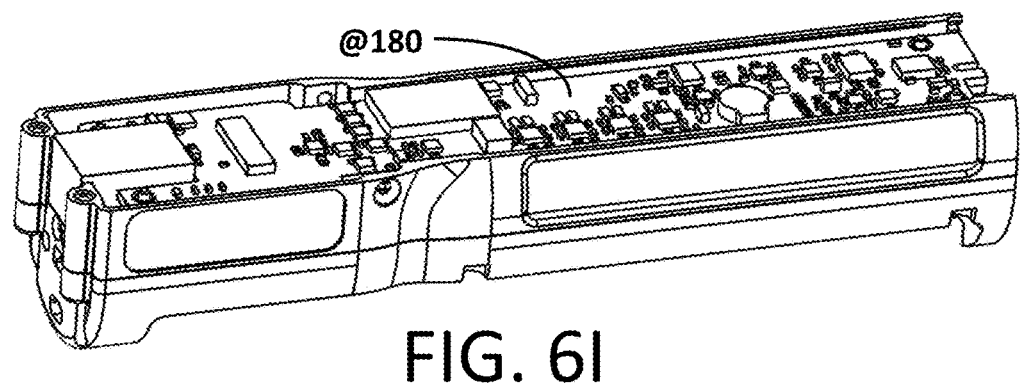

At step @508 the third and final electronics board, the Driver Board @130, is placed on top of the assembly as shown in FIG. 6I. The mounting holes of the driver board can be aligned with the threaded rods of the male-male standoffs. There are three sets of electrical connectors that need to mate in order for the boards to be fully in place. The spacers that were placed on top of the channel board will keep the boards spaced precisely the distance required by the board to board connectors.

Figure 6J:
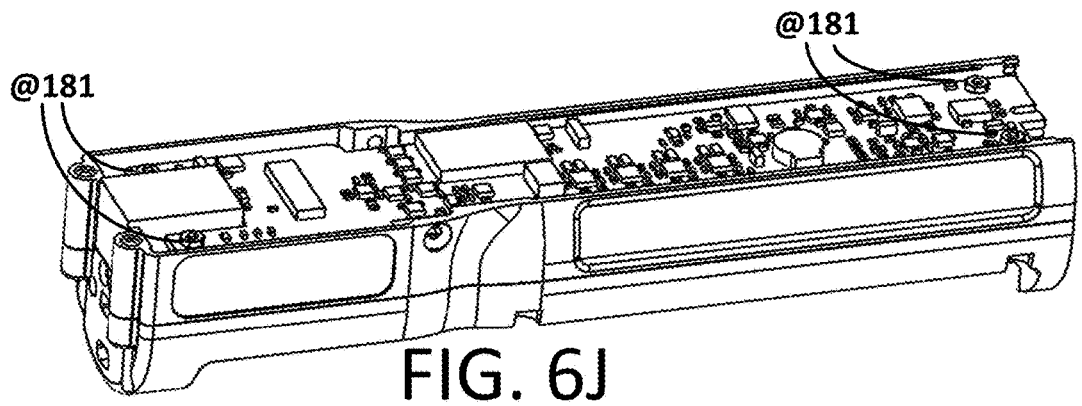

At step @509 the four threaded rods of the male-male standoffs can each be terminated with a nut @178 as shown in FIG. 6J. A thread locking compound should be applied to the threads of the connection before tightening down the nut; this prevents the nuts from coming loose over time and possibly causing electrical shorts. The nuts, once tightened down, ensure a reliable electrical connection between all the boards in the electronics stack by compressing them together.

Figure 6K:
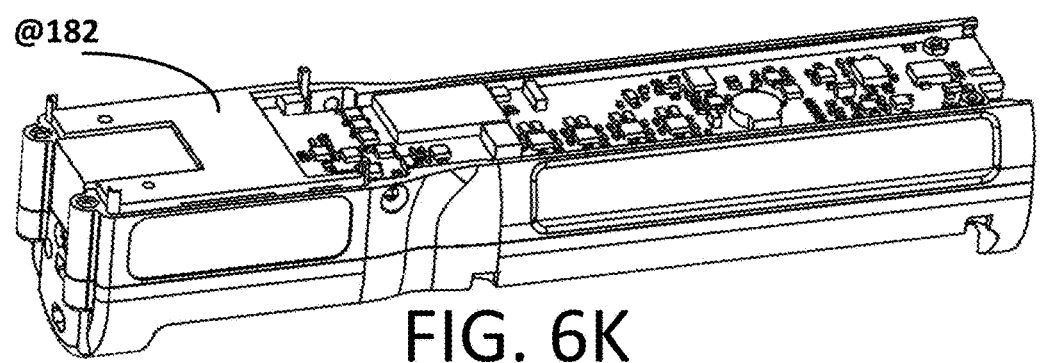

At step @510 a Screen Guide @179 is placed on the Driver Board which holds the screen display in the correct position. The screen guide is a plastic guide that fits into several alignment features in the housing and on the electronics boards as shown in FIG. 6K. This guide makes sure that the display will be positioned in the correct spot and not slide around once the case has been sealed.

Figure 6L:
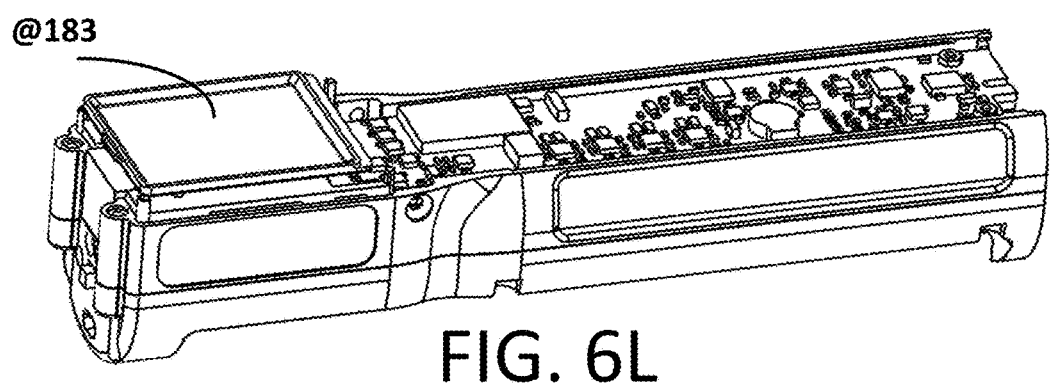

At step @511 a TFT Screen @180 is placed on Screen Guide @179 as shown in FIG. 6L. The screen makes its electrical connection to the driver board by connecting the flex cable on the screen to the zero insertion force connector on the driver board. Also mounted on the screen is a beveled border piece which provides a clean looking border for the display once the housing is sealed.

Figure 6M:
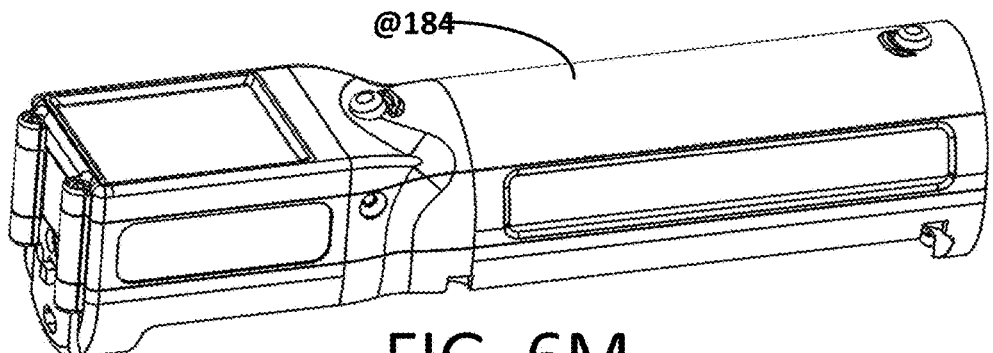

At step @512 the cover section of the housing @181 is placed over the driver board and the screen as shown in FIG. 6M. The cover must be slid into position at a 45 degree angle from the sensor side of the instrument to engage the retention clips before lowering the cover down over the driver board. There are also rectangular posts on the cover section that need to align with a corresponding feature on the section of the housing with the cross plate. Once the cover section is in position it is fastened down the rest of the housing using two screws through the top of the housing located by the screen and two more screws through the side of the housing.

Figure 6N:
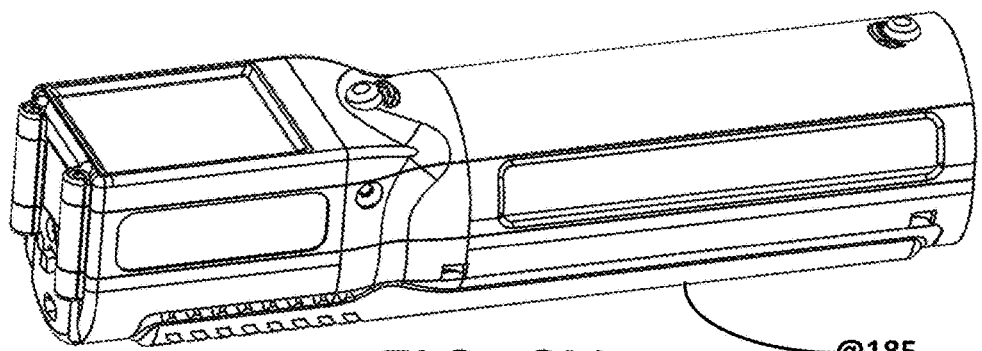
Figure 6O:
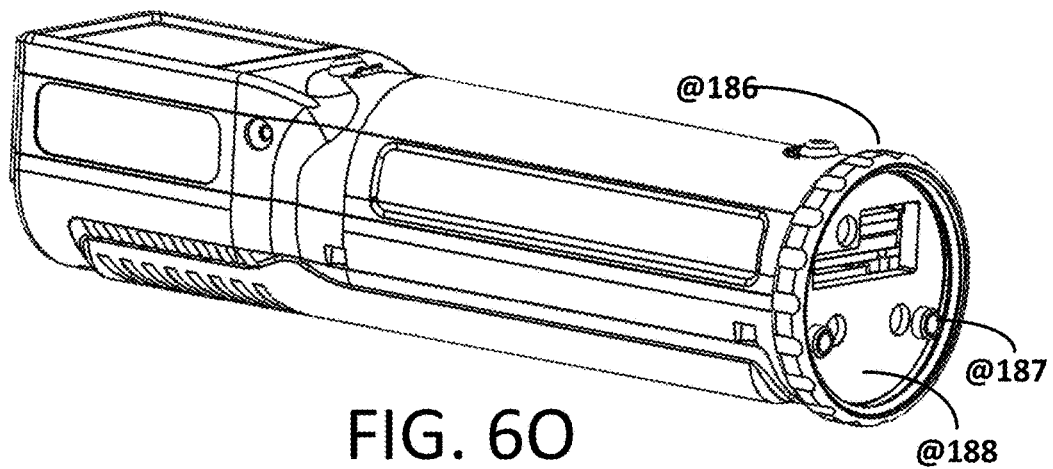

At step @513 a rear cover @182 is connected to the structural section of the housing to cover the compartment for the optional energy storage unit. The cover is keyed with an alignment feature that prevents the cover from being connected in the wrong orientation. Once the cover is resting in place it is secured with three screws into the structural section of the housing as shown in FIG. 6N. It is important that the cover is not installed until this step in the process since it covers the screw holes needed to secure the structural section of the housing to the section with the cross plate.

At step @514 a threaded ring @183 is placed on the sensor connector end of the instrument which is used to connect the instrument to any number of modular sensor tips. The ring is then held in place by a retention plate @185 which connects to the housing of the instrument with the use of three screws as shown in FIG. 6O. The retention plate is fixed tightly against the instrument but there is clearance such that the ring can still spin freely. The retention plate also features alignment posts @184 that correspond to features on the modular sensor tips to guarantee appropriate alignment of the electrical connectors.

Figure 6P:
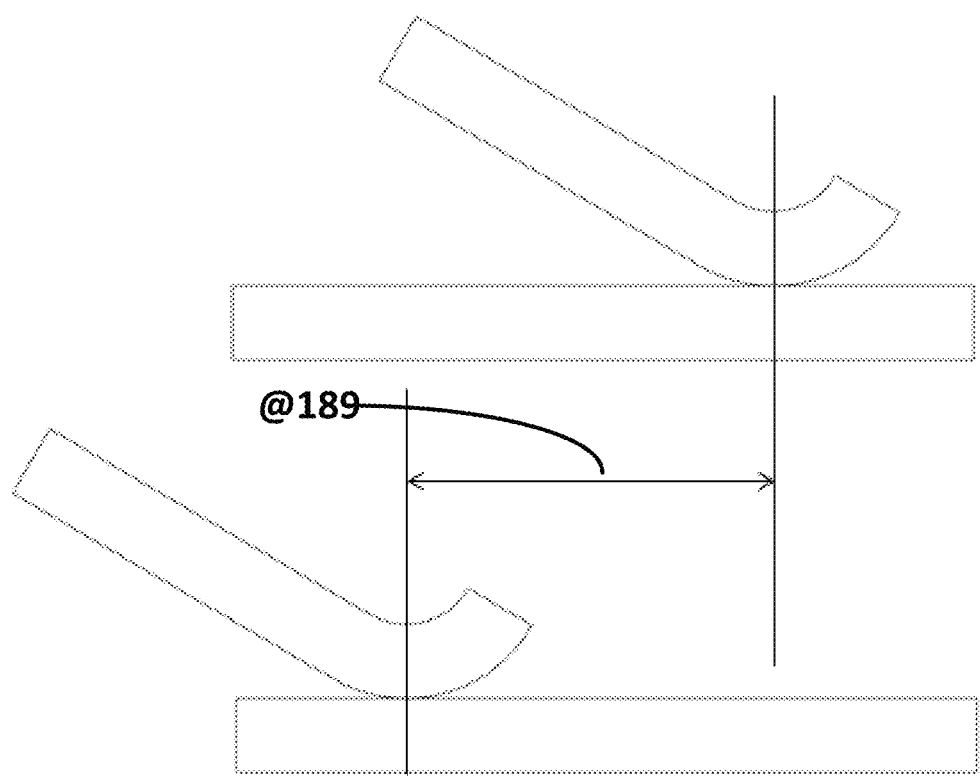

The sensor tip connection mechanism is designed such that it comprises both an electrical connection via the electronics board mounted connectors and a mechanical connection via the threaded ring. This arrangement ensures that the electrical connection remains constant as long as the threaded ring is tightened down all the way. The linear motion of the threading process also ensures that the connectors mate in a perfectly flat orientation which is important for the lifespan of electrical connectors and for reducing the risk of inadvertent electrical short circuits. This connection scheme also reduces the risk of damage from mechanical shock to the sensor end of the instrument by directing the load through the housing rather than the electronics boards. This is accomplished by mating the electrical connectors far enough that they provide a reliable electrical connection but not so far that they are bottomed out. Electrical connectors offer a specification called electrical wipe @186 which specifies a range of mating distances for which a reliable electrical connection is guaranteed, this concept is shown in FIG. 6P. By keeping the mating distance on the lower end of this range when the mechanical ring connection is bottomed out there is room for the sensor connector to move under mechanical load before transferring the force to the electronics board stack. Conversely the mechanical connection has no clearance to move within and the force will be directed into the sturdy housing.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An apparatus comprising:
   a housing that is substantially cylindrical;
   a board stack of at least two electronic boards within the housing, the board stack configured to drive an electrical signal in at least one drive channel and measuring responses from at least two sensing channels;
   a communication module configured to provide the responses to a processor; and
   an instrument side sensor connector, located at one end of the housing, operably connected to the board stack.

2. The apparatus of claim 1, further comprising a sensor mechanism having a sensor and a threaded mechanical feature.

3. The apparatus of claim 2, further comprising:
   a ring on the housing mechanically attaching the sensor mechanism, the ring having a retention plate with a pin for aligning a sensor side sensor connector with the instrument side sensor connector.

4. The apparatus of claim 3, wherein the sensor mechanism is secured to the housing by the ring mating the sensor side sensor connector with the instrument side sensor connector such that an insertion between connectors is between 20% and 80% of a wipe length associated with said connectors.

5. The apparatus of claim 1, wherein the housing comprises
   a cover section having a first hole for a display; and
   a structural section having a plurality of mounting holes, the board stack mechanically secured to the plurality of mounting holes via fasteners.

6. The apparatus of claim 5, further comprising:
   an energy storage device for powering the apparatus, and wherein
   the board stack includes an energy storage device management circuit, and
   the housing further comprises a bottom cover section securing the energy storage device.

7. The apparatus of claim 5, wherein the housing further comprises a third section having side panels running along a longer dimension of the board stack and a crossing plate configured to channel heat away from temperature sensitive components, the crossing plate fit between a first and a second electronics board in the board stack.

8. The apparatus of claim 7, further comprising a gap pad adhered to the crossing plate and contacting at least one component on the first electronics board.

9. The apparatus of claim 1, wherein the outer diameter of the housing is less than 2.5 inches.

* * * * *